(12) United States Patent
Buck

(10) Patent No.: US 10,939,913 B1
(45) Date of Patent: Mar. 9, 2021

(54) ANASTOMOTIC COUPLER

(71) Applicant: Donald W. Buck, St. Louis, MO (US)

(72) Inventor: Donald W. Buck, St. Louis, MO (US)

( * ) Notice: Subject to any disclaimer, the term of this patent is extended or adjusted under 35 U.S.C. 154(b) by 0 days.

(21) Appl. No.: 16/950,209

(22) Filed: Nov. 17, 2020

Related U.S. Application Data

(60) Provisional application No. 63/061,303, filed on Aug. 5, 2020, provisional application No. 62/936,868, filed on Nov. 18, 2019.

(51) Int. Cl.
*A61B 17/11* (2006.01)

(52) U.S. Cl.
CPC ........... *A61B 17/11* (2013.01); *A61B 17/1114* (2013.01); *A61B 2017/1107* (2013.01); *A61B 2017/1132* (2013.01); *A61B 2017/1139* (2013.01)

(58) Field of Classification Search
CPC ......... A61B 17/1114; A61B 2017/1107; A61B 2017/1132
See application file for complete search history.

(56) References Cited

U.S. PATENT DOCUMENTS

| | | | | |
|---|---|---|---|---|
| 2004/0054405 | A1* | 3/2004 | Richard | A61B 17/0643 623/1.36 |
| 2008/0114385 | A1* | 5/2008 | Byrum | A61B 17/1227 606/154 |
| 2013/0267968 | A1* | 10/2013 | Ferlin | A61B 17/1285 606/145 |
| 2019/0150928 | A1* | 5/2019 | Boiman | A61B 17/1114 |
| 2020/0337707 | A1* | 10/2020 | Ad-El | A61B 17/06066 |

* cited by examiner

*Primary Examiner* — Wade Miles
(74) *Attorney, Agent, or Firm* — Polsinelli PC

(57) ABSTRACT

An anastomotic coupler is provided. A ring forms an aperture operable to receive a tubular structure. The ring can include a plurality of receiving portions. A fixation device includes a housing and a cartridge. The cartridge includes a plurality of fasteners, and the housing is operable to receive the tubular structure such that the cartridge is inserted into a lumen of the tubular structure. The ring is aligned with the cartridge such that the receiving portions are aligned with the fasteners. Upon actuation of the fixation device, the fasteners puncture the tubular structure radially outward from the lumen and are received by the receiving portions such that the tubular structure is coupled with the ring.

18 Claims, 10 Drawing Sheets

ANASTOMOTIC COUPLER

CROSS-REFERENCE TO RELATED APPLICATIONS

This application claims the benefit of U.S. Provisional Patent Application No. 62/936,868, filed in the U.S. Patent and Trademark Office on Nov. 18, 2019, and U.S. Provisional Patent Application No. 63/061,303, filed in the U.S. Patent and Trademark Office on Aug. 5, 2020, each of which is incorporated herein by reference in its entirety for all purposes.

FIELD

The present disclosure relates generally to an anastomotic coupler. In at least one example, the present disclosure relates to a surgical system and method to utilize an anastomotic coupler to connect two tubular structures such as vessels, esophagus, intestine, lymphatic structure, and/or graft material.

BACKGROUND

An anastomosis is a connection between two luminal structures. Commonly, these connections can occur with blood vessels (for example, vascular anastomosis), or tubular gastrointestinal structures (for example, intestines, stomach, esophagus). Conventional techniques allow the anastomosis to be completed between two ends (referred to as end-to-end anastomosis), or between the end of one structure and the side of another structure (referred to as end-to-side anastomosis). Procedures requiring these anastomoses are carried out thousands of times per day, globally. Likewise, multiple surgical specialties rely upon the creation of reliable, unobstructed anastomoses for successful treatment of their respective patients.

BRIEF DESCRIPTION OF THE DRAWINGS

Implementations of the present technology will now be described, by way of example only, with reference to the attached figures, wherein.

DETAILED DESCRIPTION

Figure 1:
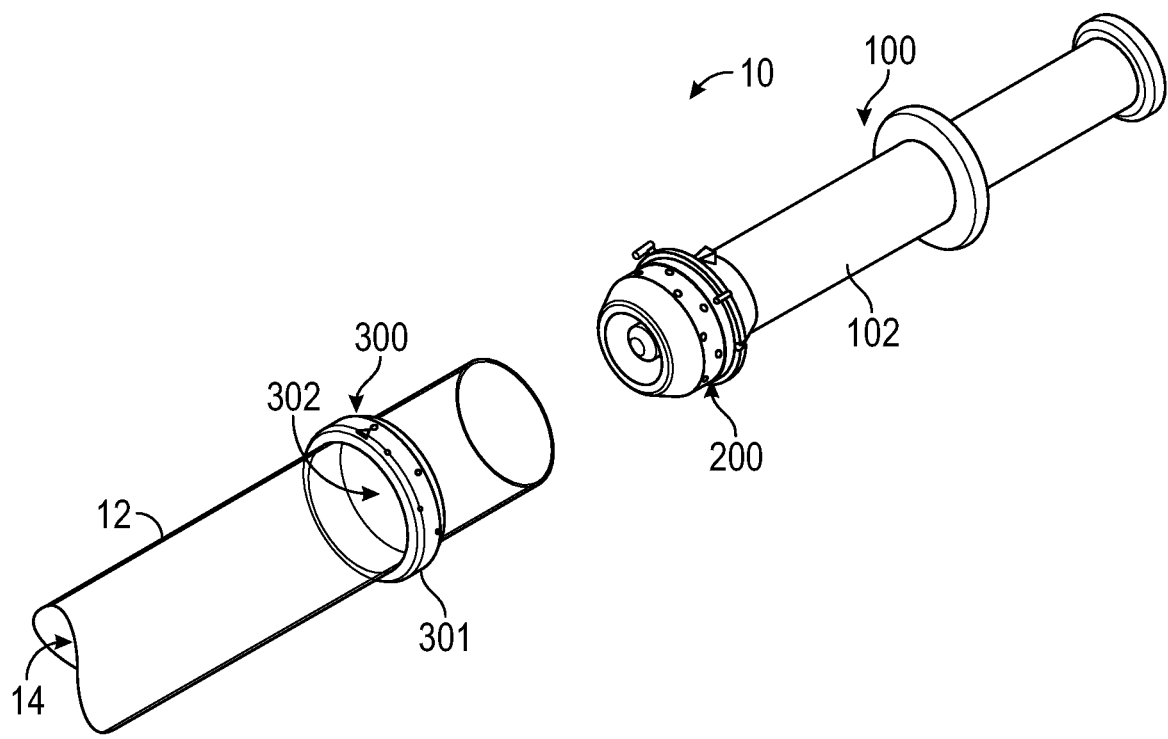
FIG. 1 illustrates a diagram of an anastomotic coupler.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the examples described herein. The drawings are not necessarily to scale and the proportions of certain parts may be exaggerated to better illustrate details and features of the present disclosure.

The original technique for vascular suture anastomoses was created by Alexis Carrel between 1901-1910. This pioneering work resulted in Carrel receiving the Nobel Prize in 1912. Despite 100 years of surgical evolution and innovation since that discovery, the majority of vascular anastomoses to this day still employ suture techniques similar to Carrel's initial description in the early 1900s. In the 1970s, gastrointestinal stapling devices were introduced, which quickly replaced primary suture techniques for bowel anastomoses. However, most surgeons still employ circumferential suture techniques in the serosal layer overlying the stapled anastomosis for added support. Although generally successful, these techniques can take long periods of time, often require additional surgical expertise, and if not performed correctly, may result in leakage (blood, stool contents, gastric contents, lymphatic fluid), constriction, stenosis, and/or obstruction at the anastomotic site. In the case of vascular anastomoses, stenosis and/or obstruction can result in catastrophic complications such as heart attack, stroke, peripheral limb ischemia, amputation, death, and reconstructive failure and soft-tissue loss. For example, in the setting of gastrointestinal anastomoses, these complications can result in extra-luminal leak of gastrointestinal contents, infection, sepsis, obstruction, and death.

With the understood importance of reliable, open anastomoses, alternatives to sutures and staples have been used. An example of a vascular anastomotic coupler is described, for instance, in U.S. Patent Pub. No. 2015/0088172 A1 (the '172 Publication). This coupler has two circular ends with spikes or pins. The vessel is brought through the ring and the vessel wall is everted, or rolled over, the pins for securement as shown in FIGS. 2A and 2B of the '172 Publication. This is completed on each vessel end, and the two rings are then brought together with the spikes/pins being forced into the opposite ring to join the ends together as shown in FIG. 1C of the '172 Publication. However, because of the potential for micro-motion of the vessels and size mismatch due to the anastomotic coupler of the '172 Publication, blood leakage may happen, and/or one of the pins may tear through the vessel wall creating a leak and/or site for platelet aggregation and thrombosis (blood clot formation). Likewise, with the anastomotic coupler of the '172 Publication, for thicker walled, less elastic vessels, particularly arteries, everting vessel edges can be quite difficult and may result in trauma to the vessel wall (intima) and/or stenosis at the anastomosis, both of which can create platelet aggregation, turbid flow, and/or thrombosis with subsequent obstruction of flow. Additionally, the technique of the '172 Publication requires additional specialized equipment (surgical microscope, high-powered loupe magnification) to use. For gastrointestinal stapled anastomoses, many procedures are performed either side-to-side which is not a natural pathway for intestinal smooth muscle propulsion of stool contents (for example, non-longitudinal flow along the length of the intestine), or end-to-end, which requires a separate, remote full-thickness bowel access incision for deployment, thereby creating a secondary weak point for potential leak, or adhesion formation.

Referring now to FIG. 1, an anastomotic coupler 10 is provided. The anastomotic coupler 10 is provided to create a connection between adjacent tubular structures 12. The tubular structure 12 can include blood vessels, grafts, prostheses, gastrointestinal structures, esophagus, lymphatics, and/or any other suitable channels of the body or the operation for which the tubular structure 12 is created. The tubular structure 12 forms a lumen 14 through which matter can be passed, for example blood, food, fluids, and/or cells.

The anastomotic coupler 10 includes a ring 300 forming an aperture 302. The ring 300 is operable to receive a tubular structure 12 through the aperture 302. While the ring 300 as illustrated in FIG. 1 has a substantially circular shape, the ring 300 can have any suitable shape such as rectangular, triangular, octagonal, hexagonal, and/or oval. Additionally, the ring 300 as illustrated in FIG. 1 is a singular solid piece, in some examples, for ease of application or manufacturing purposes, the ring 300 can include two semi-circular or arc-type pieces that are joined together around the tubular structure 12.

The size of the lumen 302 of the ring 300 can vary based on the application and the size of the tubular structure 12. For example, the diameter of the lumen 302 can range from about 0.5 millimeters (mm) (for example for lymphatic connections) to about 60 millimeters (for example for gastrointestinal connections). Due to the range of diameters for the ring 300, and the range of diameters for the tubular structure 12, the appropriate ring 300 can be selected by measuring the internal diameter of the tubular structure 12. This can be accomplished, for example, with an intraluminal measurement guide/device. If there is a significant size mismatch (1 mm or greater) between the tubular structure 12 and the ring 300, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

Figure 2:
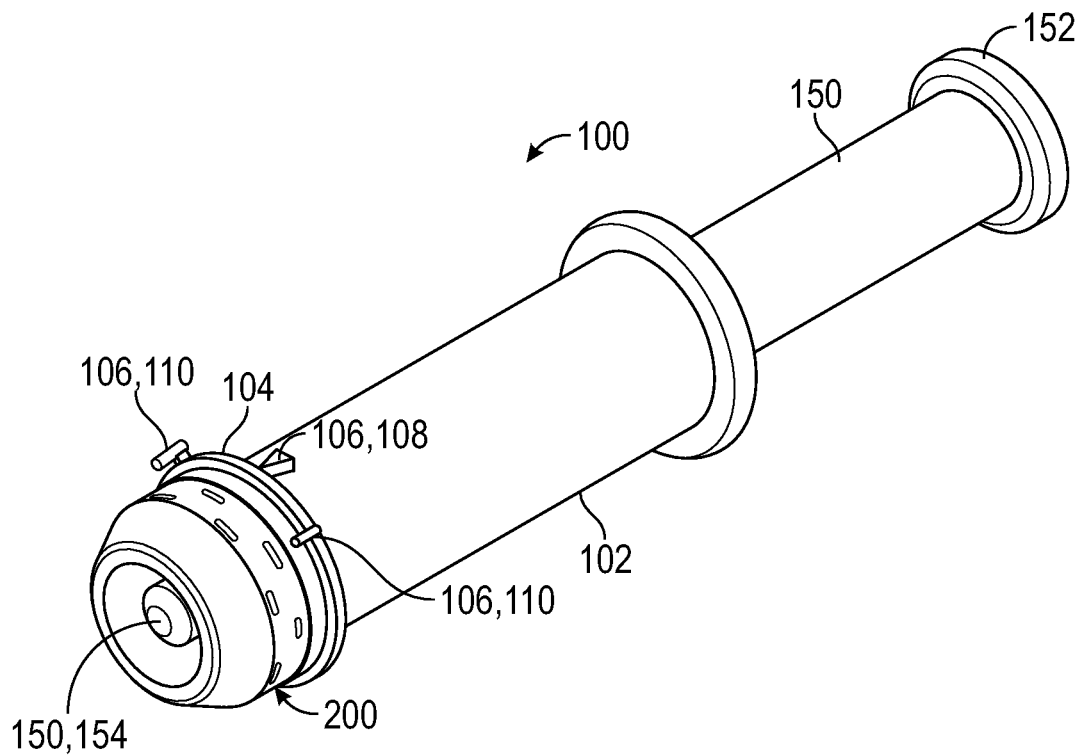
FIG. 2 illustrates a fixation device.

Referring also to FIG. 2, the anastomotic coupler 10 also includes a fixation device 100. The fixation device 100 is operable to couple the tubular structure 12 with the ring 300. The fixation device 100 can include a housing 102 and a cartridge 200. The cartridge 200 includes a plurality of fasteners 206 (as shown in FIGS. 5-10B). The fasteners 206 are operable to puncture the tubular structure 12 and be partially received in the ring 300 to couple the tubular structure 12 with the ring 300. In at least one example, the cartridge 200 can be removably coupled with the housing 102. Accordingly, the cartridge 200 may be replaceable to allow multiple uses of the fixation device 100. In some examples, the cartridge 200 may not be removable such that the fixation device 100 is provided for a one-time use. The fixation device 100 can include an actuation mechanism operable to actuate the fixation device 100 to drive the fasteners 206 from the cartridge 200. As illustrated, in at least one example, the actuation mechanism can include a pusher rod 150. Upon actuation of the fixation device 100, the pusher rod 150 can translate along a longitudinal axis upon receiving a force. In some examples, the actuation mechanism can include a manually activated mechanism, a spring activated mechanism, a screw mechanism, and/or any other suitable mechanism to drive the fasteners 206 from the cartridge 200. For example, the pusher rod 150 may translate along the longitudinal axis upon receiving a manual force from a user physically pushing the pusher rod 150. In another example, the pusher rod 150 may translate along the longitudinal axis upon receiving a force from a spring. The spring may be released to push the pusher rod 150 upon a user pressing a button or a switch.

Figure 3:
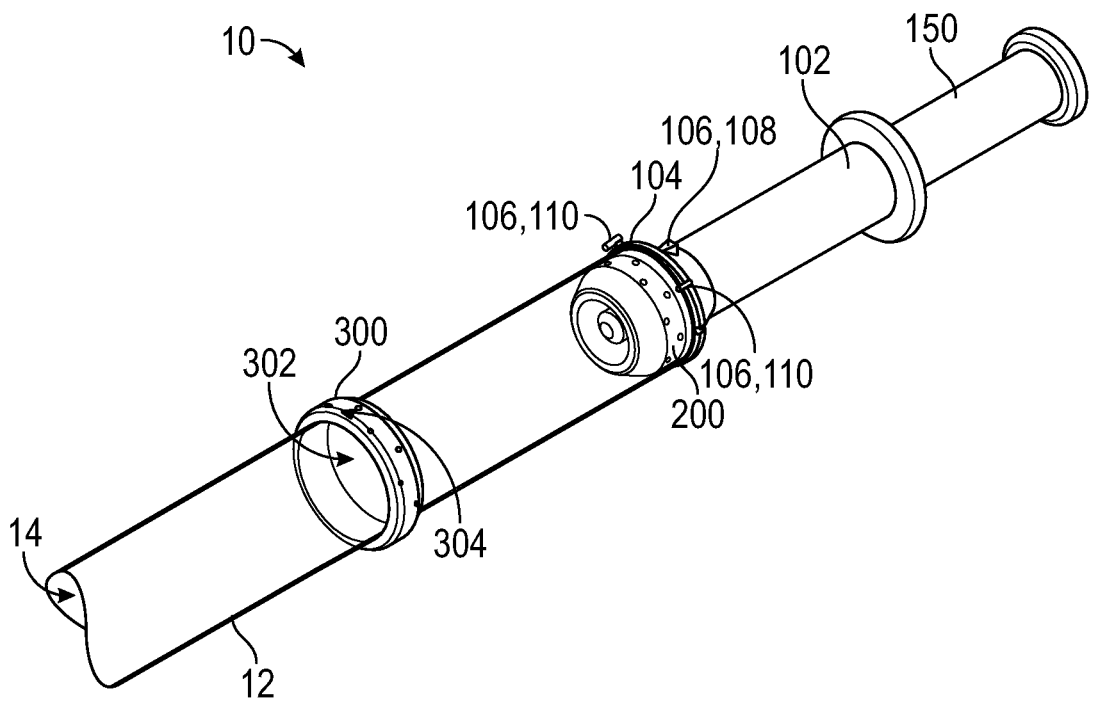
FIG. 3 illustrates a tubular structure being received by a fixation device.

The fixation device 100 includes stop 104 to receive the tubular structure 12. In at least one example, the stop 104 can be formed as a portion of the cartridge 200 to ensure alignment with the cartridge 200. In some examples, the stop 104 can be formed as a portion of the housing 102. The stop 104 extends radially from the housing 104 such that a free end of the tubular structure abuts the stop 104. As illustrated in FIG. 3, the housing 102 receives the free end of the tubular structure 12 such that the cartridge 200 is inserted into the lumen 14 of the tubular structure. When correctly positioned, the free end of the tubular structure 12 abuts the stop 104. The stop 104 ensures the placement and alignment of the ring 300, the cartridge 200, and the free end of the tubular structure 12. The alignment of the ring 300, the cartridge 200, and the free end of the tubular structure 12 is critical to ensure adequate connection between the tubular structure 12 and another tubular structure 12.

Figure 4:
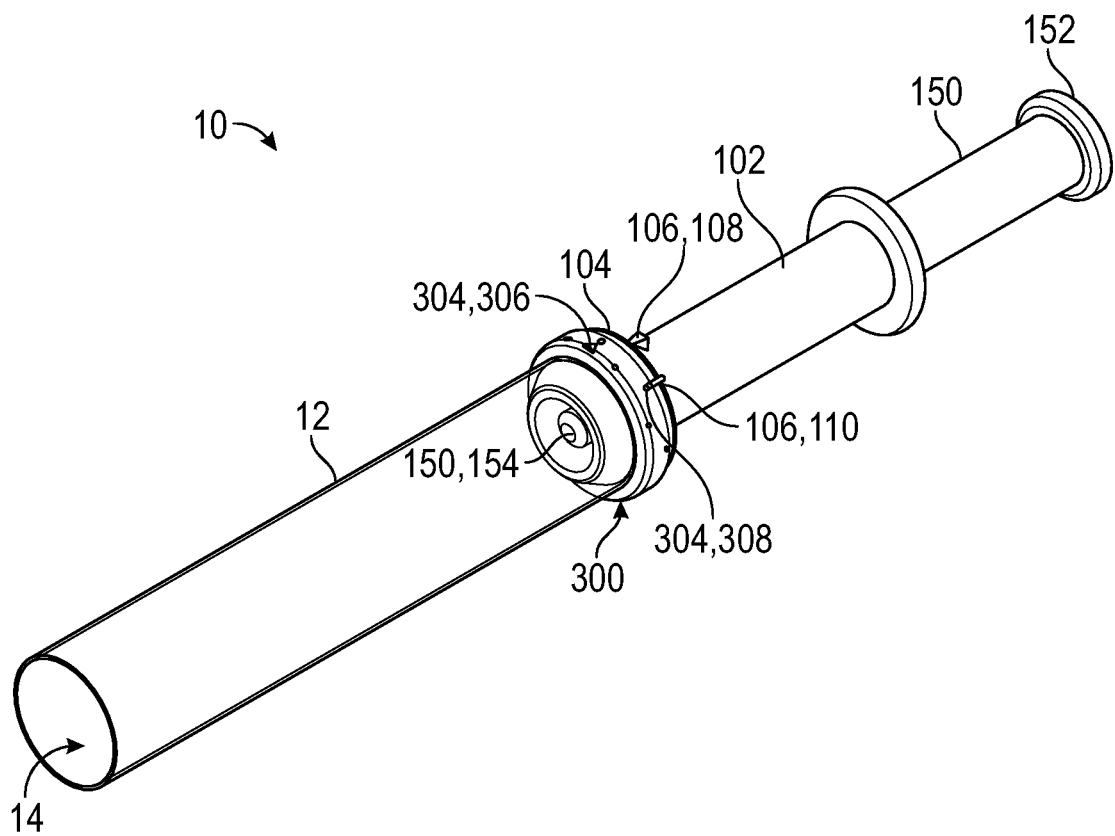
FIG. 4 illustrates a ring being aligned with a cartridge of the fixation device.

As illustrated in FIG. 4, after the tubular structure 12 is received by the fixation device 100 and abuts the stop 104, the ring 300 can be positioned to abut the stop such that the ring 300 is aligned with the free end of the tubular structure 12.

The stop 104 can include a plurality of alignment components 106 which correspond with alignment components 304 of the ring 300. Accordingly, when the ring 300 is aligned and/or correctly positioned, the alignment components 106 of the stop 104 are aligned with the alignment components 304 of the ring 300. In some examples, the alignment components 106, 304 can include one or more alignment markers 108, 304. The alignment markers 108, 304 can be shaped, for example as triangles. Accordingly, to align the ring 300, the tips of the triangles for the alignment markers 108, 304 can point towards one another. In some examples, the alignment components 106, 304 can include one or more alignment pins 110 and corresponding alignment receivers 308. When the ring 300 is aligned, the alignment pins 100 can be received by the alignment receivers 308. While the figures illustrate the alignment pins 100 being disposed on the fixation device 100 and the alignment receivers 308 being disposed on the ring 300, in some examples, the alignment pins 100 may be disposed on the ring 300 and the alignment receivers can be disposed on the fixation device 100.

Figure 5:
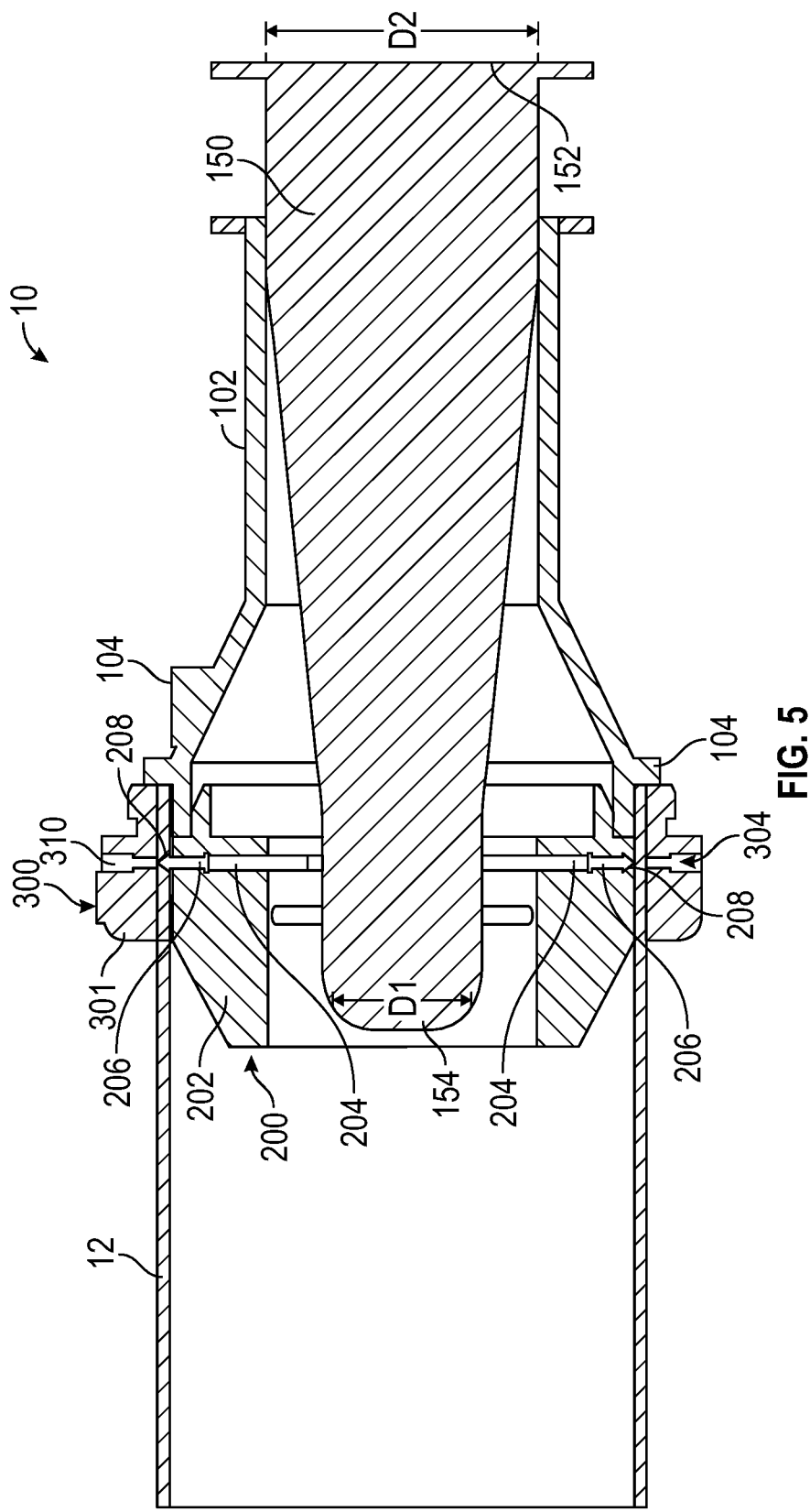
FIG. 5 illustrates a cross-sectional view of FIG. 4.

FIG. 5 illustrates a cross-sectional view of the tubular structure 12, the ring 300, and the cartridge 200 aligned. In addition to ensuring the ring 300 aligns with the free end of the tubular structure 12, the ring 300 is aligned with the cartridge 200. When the ring 300 is properly aligned with the cartridge 200, a plurality of receiving portions 310 of the ring 300 are aligned with the plurality of fasteners 206 of the cartridge 200.

Figure 6:
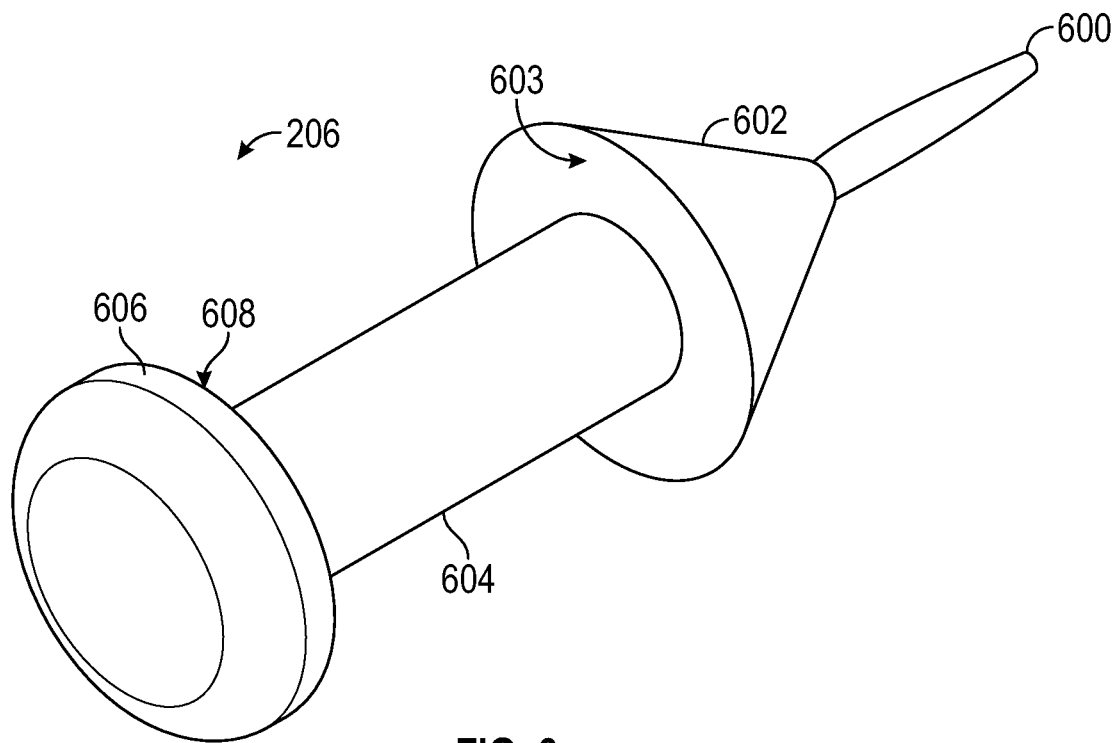
FIG. 6 illustrates an exemplary fastener.
Figure 7:
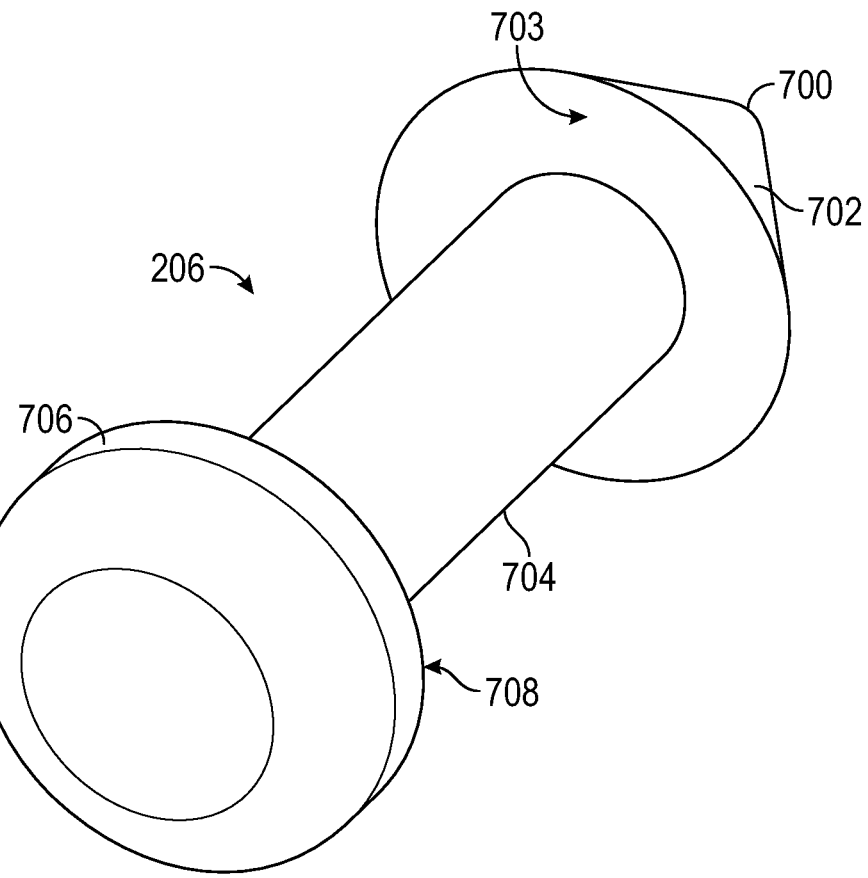
FIG. 7 illustrates another example of a fastener.
Figure 8:
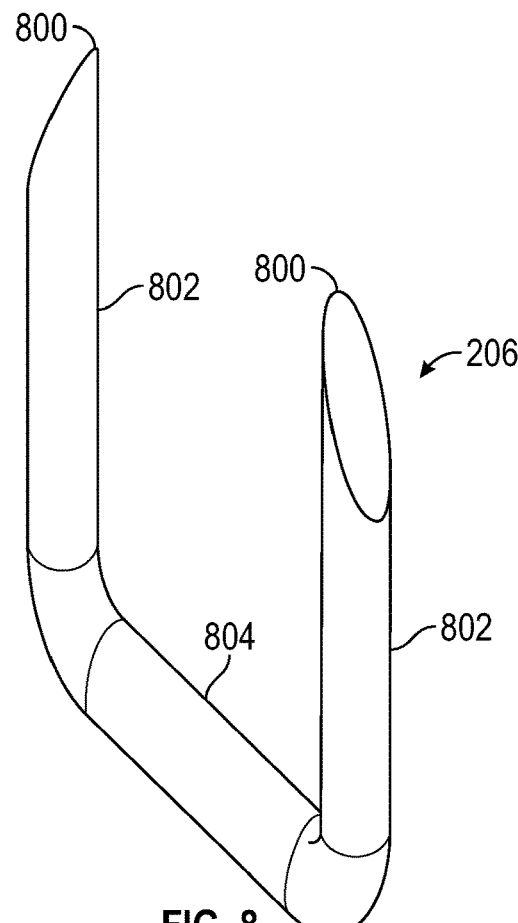
FIG. 8 illustrates another example of a fastener.

The fasteners 206 can be any suitable fastener 206 to couple the ring 300 with the tubular structure 12 and prevent movement between the ring 300 and the tubular structure 12. For example, the fasteners 206 can include, but are not limited to, tacks 600, 700 (as shown in FIGS. 6 and 7), staples 800 (as shown in FIG. 8), pins, adhesive, internal ring, internal mesh, wire, clamp, coil, and/or suture. Other suitable mechanisms to couple the ring 300 with the tubular structure 12 can be utilized without deviating from the scope of the present disclosure.

As illustrated in FIG. 6, the tack 600 can include a puncturing portion 602 which is operable to puncture the tubular structure 12. An abutment surface 603 abuts against a surface of the corresponding receiving portion 310 of the ring 300. A body 604 spans the thickness of the wall of the tubular structure 12, and an end 606 includes an abutment surface 608 which abuts against the inner surface of the tubular structure 12. The abutment surfaces 603, 608 prevent the fastener 206 from being removed from the tubular structure 12 and the ring 300.

As illustrated in FIG. 7, the tack 700 can include a puncturing portion 702 which is operable to puncture the tubular structure 12. The exemplary tack 700 does not include as long of a puncturing portion 702 as the puncturing portion 602 as illustrated in FIG. 6. An abutment surface 703 abuts against a surface of the corresponding receiving portion 310 of the ring 300. A body 704 spans the thickness of the wall of the tubular structure 12, and an end 706 includes an abutment surface 708 which abuts against the inner surface of the tubular structure 12. The abutment surfaces 703, 708 prevent the fastener 206 from being removed from the tubular structure 12 and the ring 300.

As illustrated in FIG. 8, the staple 800 can include two puncturing portions 802 which are operable to puncture through the tubular structure 12 and be received in the corresponding receiving portion 310 of the ring 300. A body 804 spans between the puncturing portions 802 and is operable to abut the inner surface of the tubular structure 12 to prevent the fastener 206 from being removed from the tubular structure 12. In at least one example, the puncturing portions 802 may be operable to bend or deform when received in the receiving portion 310 to prevent the puncturing portions 802 from being removed from the ring 300, ensuring coupling of the tubular structure 12 with the ring 300.

Figure 9:
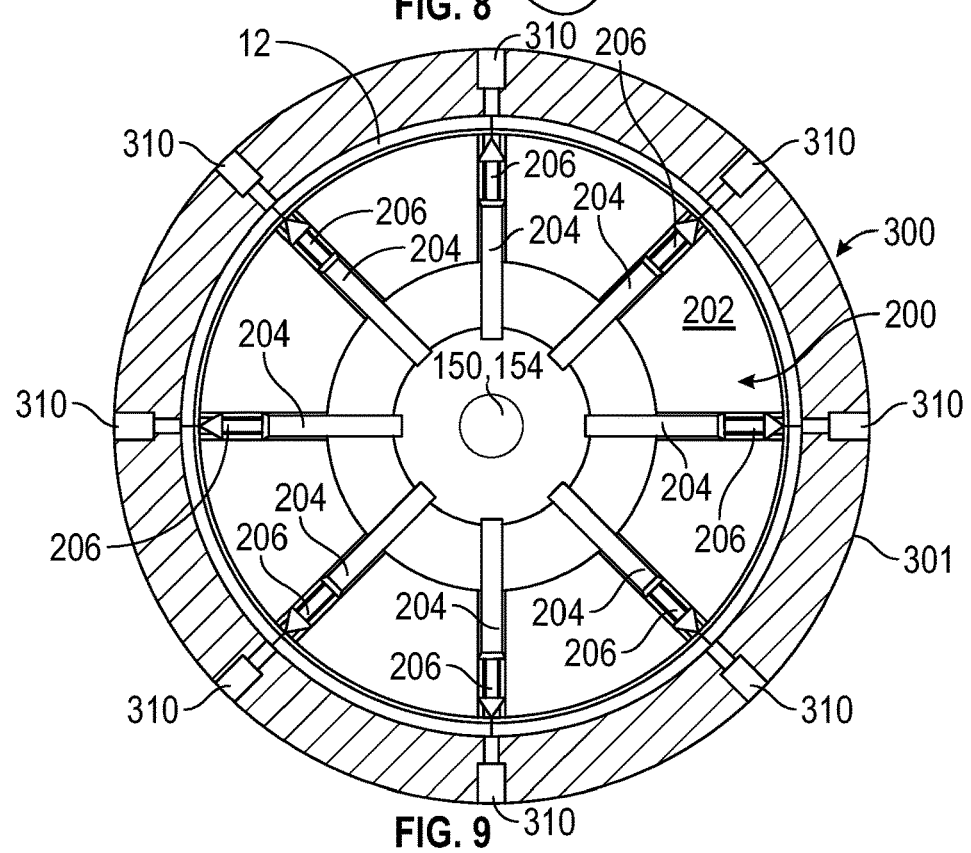
FIG. 9 illustrates a cross-sectional view of the cartridge aligned with the ring.

Referring to FIGS. 5 and 9, the cartridge 200 can include a plurality of drivers 204 corresponding with the plurality of fasteners 206. Upon actuation of the fixation device 100, the drivers 204 activate to push the corresponding fasteners 206 radially outward from the cartridge 200. The drivers 204 may include rods which abut the fasteners 206 and towards the center of the body 202 of the cartridge 200. In some examples, the drivers 204 may be spring loaded.

The pusher rod 150, as illustrated in FIG. 5, is tapered from a front portion 154 with a smaller diameter D1 to a rear portion 152 with a larger diameter D2 which is greater than the smaller diameter D1. The drivers 204 may abut the fasteners 206 on one end while extending into the cartridge 200 so that the opposing end of the fasteners 206 abut the pusher rod 150.

Figure 10A:
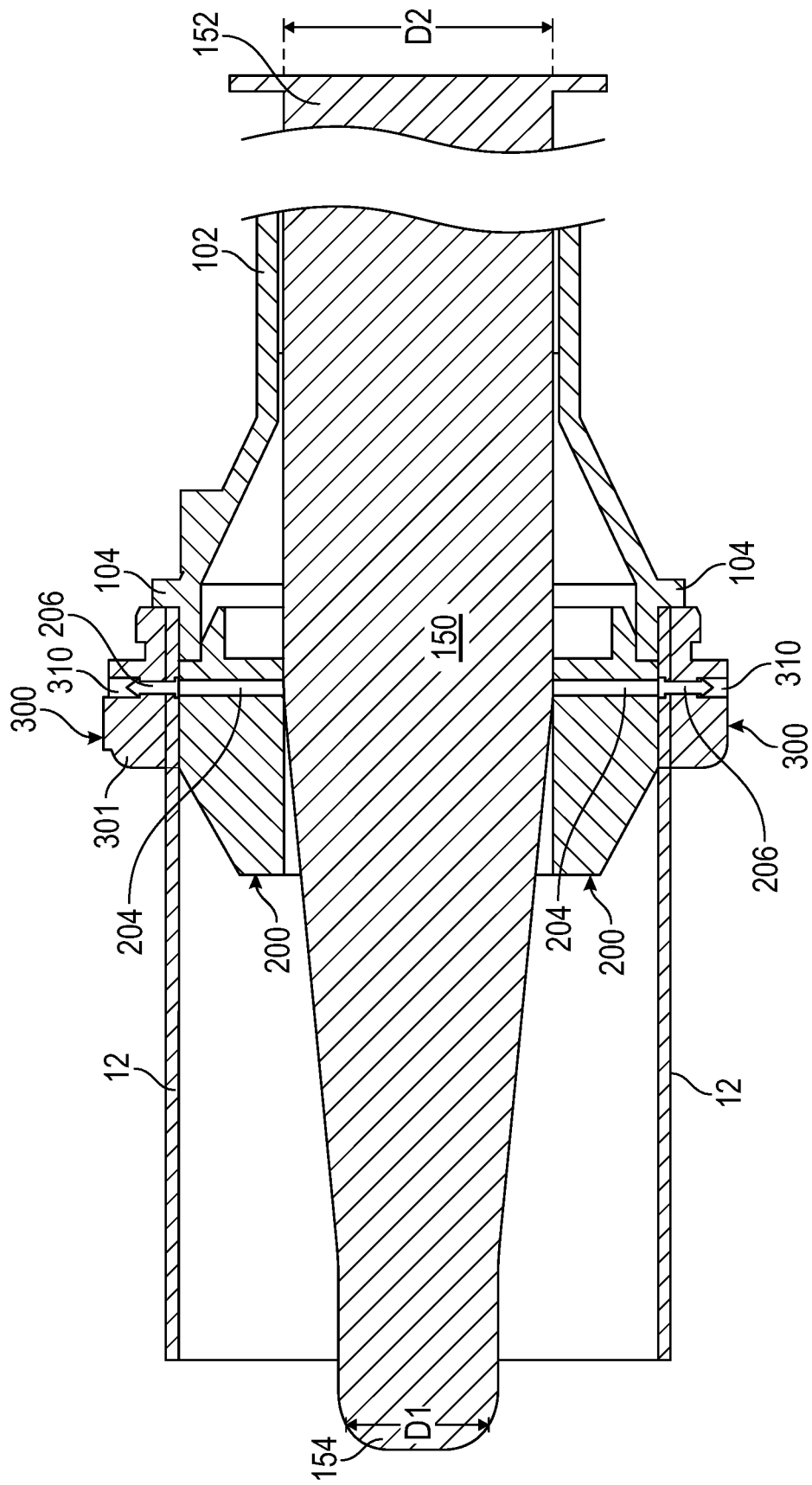
FIG. 10A illustrates actuation of the fixation device.
Figure 10B:
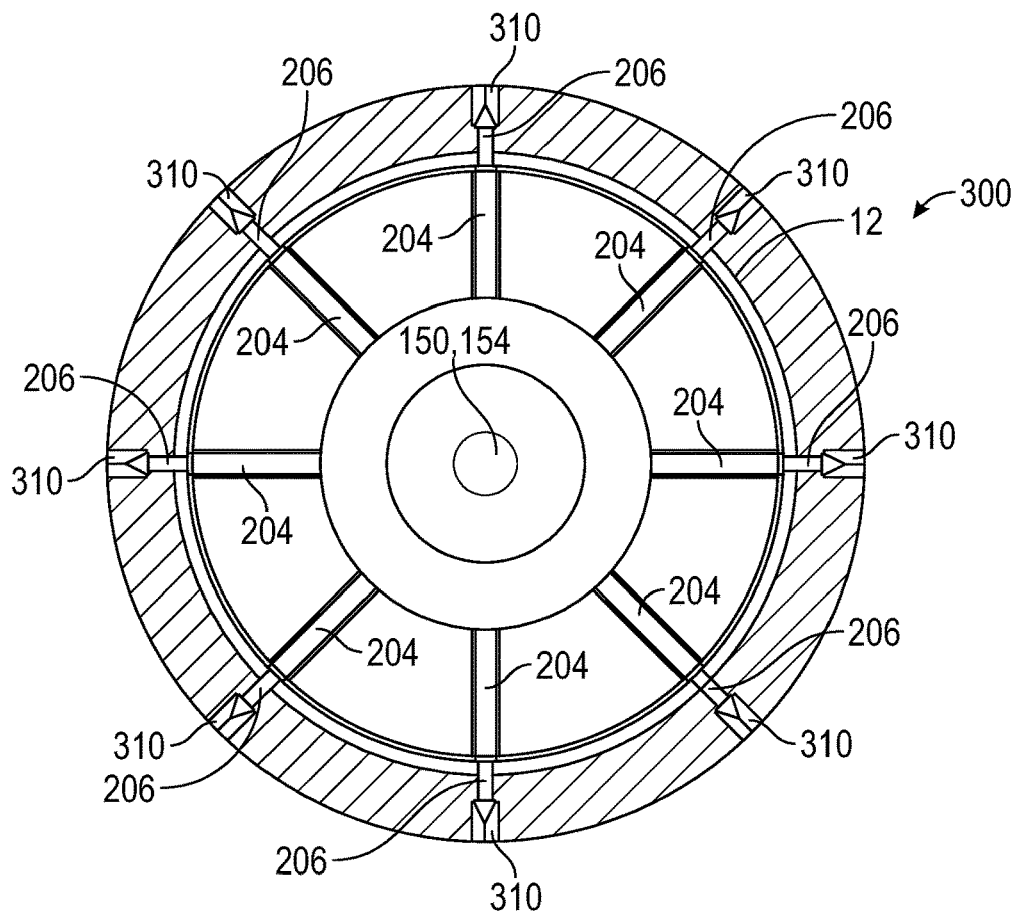
FIG. 10B illustrates a cross-sectional view of FIG. 10A.

Referring to FIGS. 10A and 10B, the fixation device 100 is actuated. Actuation of the fixation device 100 can include translating the pusher rod 150 along the longitudinal axis through the cartridge 200 from the front portion 154 towards the rear portion 152. The pusher rod 150, increasing in thickness, then activates the drivers 204 to drive the fasteners 206 radially outward from the cartridge 200, through the tubular structure 12, and into the receiving portions 310 of the ring 300. Once the ring 300 is coupled with the tubular structure 12, the fixation device 100 can be removed from the tubular structure 12. The ring 300 is then affixed or secured to the end of the tubular structure 12, maintaining the structure of the lumen of the tubular structure 12.

The fixation device 100, the ring 300, and/or the fasteners 206 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. Other materials may be used without deviating from the scope of the present disclosure so long as the material is biocompatible and have sufficient strength and durability. The fixation device 100, the ring 300, and/or the fasteners 206 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin).

Figure 11:
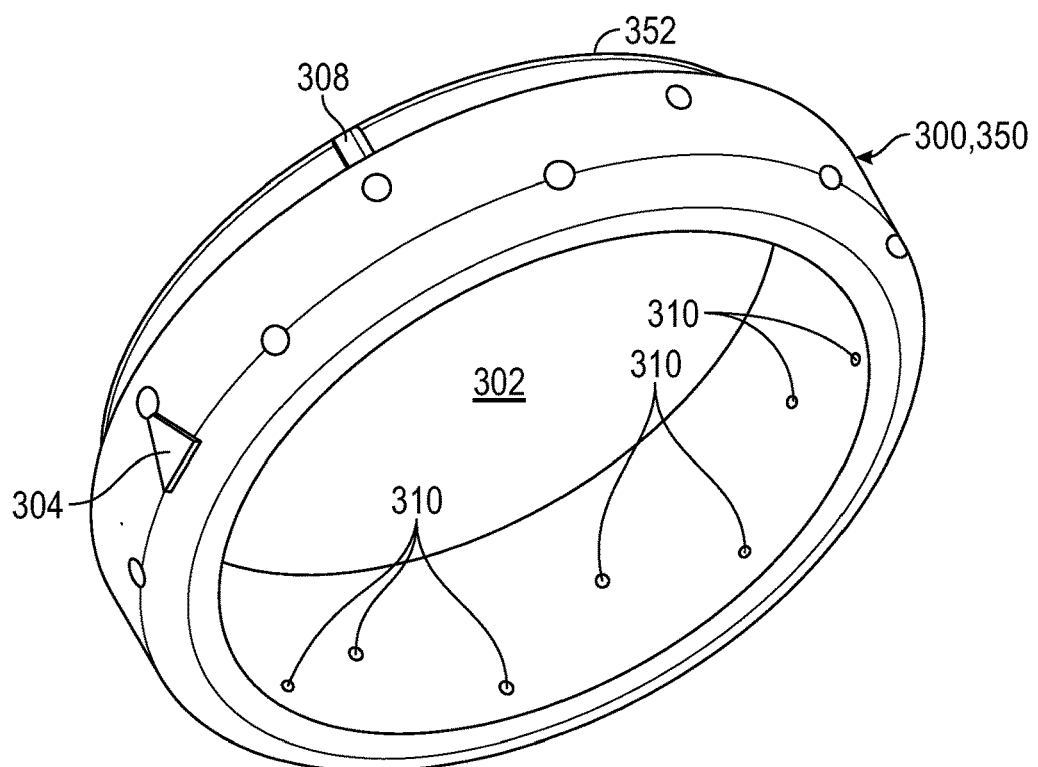
FIG. 11 illustrates an exemplary ring.
Figure 12:
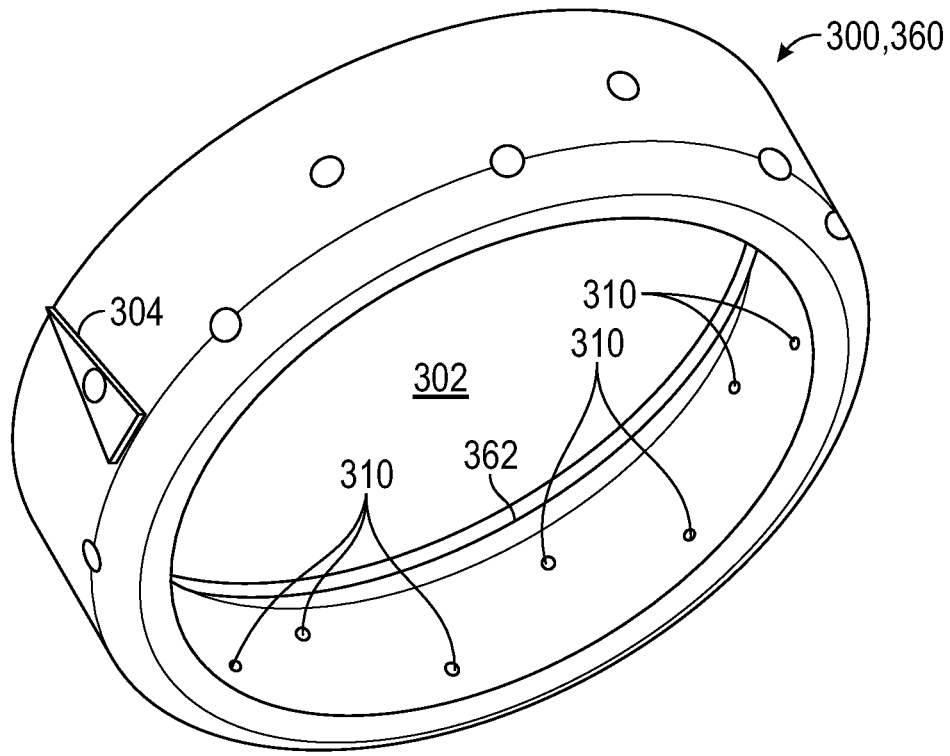
FIG. 12 illustrates an example of another ring.

The above process of coupling the ring 300 with the tubular structure 12 can be repeated for a second tubular structure 12 with a second ring 300. For example, FIG. 11 illustrates an exemplary male ring 350, and FIG. 12 illustrates an exemplary corresponding female ring 350. Similar to the ring 300 discussed above, the male ring 350 and the female ring 360 each include an aperture 302 operable to receive a tubular structure 12, receiving portions 310 operable to receive the fasteners 206, and alignment portions 304, 308. The male ring 350 includes a mating portion 352, and the female ring 360 includes a corresponding mating portion 362. The mating portion 352 is operable to couple with the mating portion 362 to couple the male ring 350 and the female ring 360 with one another. As illustrated in FIGS. 11 and 12, the mating portion 352 of the male ring 350 extends from the ring 350 and is operable to be received by the mating portion 362 of the female ring 360. In some examples, the rings 300 can be coupled with one another by, for example, fastening, snapping, clamping, tacking, pinning, loop and hook, adhesive, and/or other connecting method so long as the rings 300 are securely coupled with one another.

Figure 13:
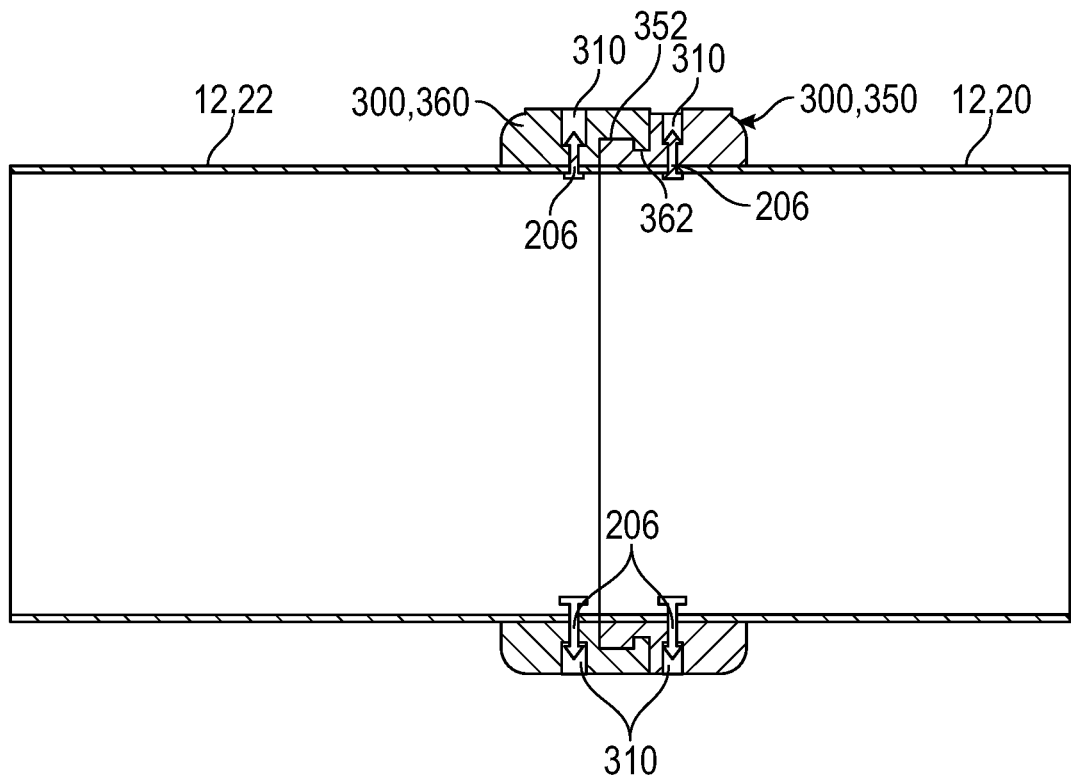
FIG. 13 illustrates a cross-sectional view of two rings coupled with one another to join two tubular structures.

As illustrated in FIG. 13, when the rings 350, 360 are coupled with one another, the lumens 14 of the two tubular structures 20, 22 are aligned in fluid communication with one another. In at least one example, the rings 350, 360 can create a seal to prevent fluid leakage. Accordingly, the anastomotic coupler 10 provides a more reliable, faster, more secure anastomotic coupling device to create a sealed, leak-proof, open connection between the ends of the tubular structures 20, 22 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction. In at least one example, the two rings 350, 360 may be joined such that the mating portion 352 of the male ring 350 telescopes a predetermined distance into the mating portion 362 of the female ring 360 to create a sufficient seal to prevent fluid leakage from the tubular structures 12 through the rings 350, 360.

Figure 14:
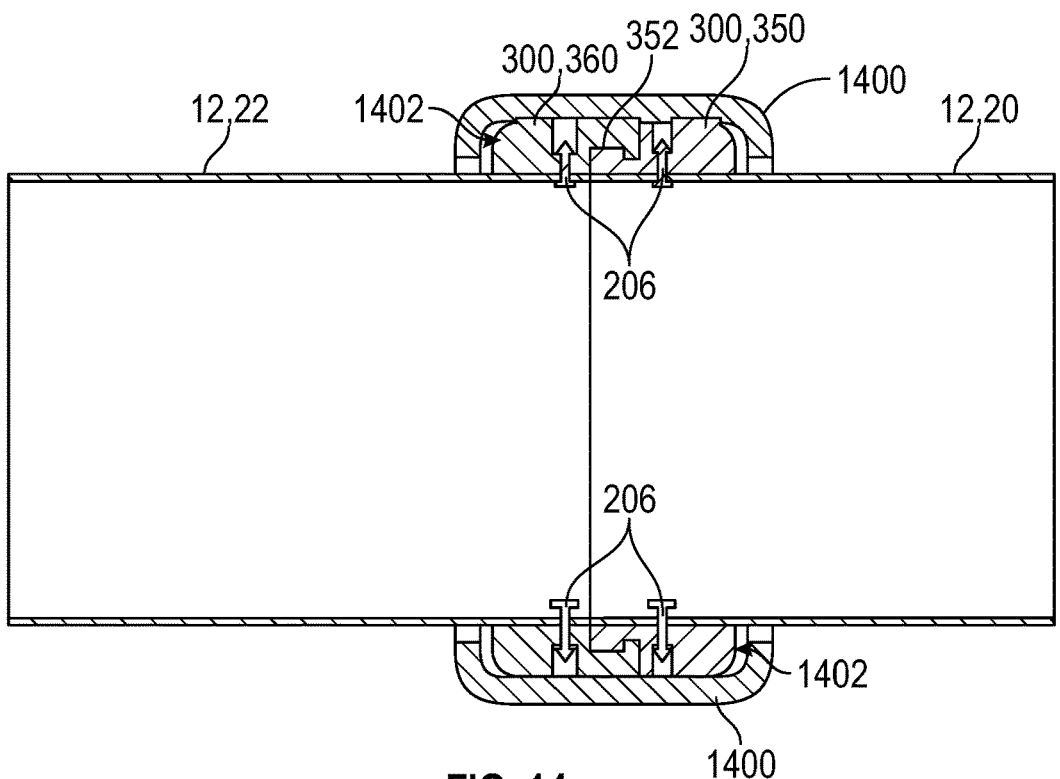
FIG. 14 illustrates a cap disposed over the two rings of FIG. 13.
Figure 15:
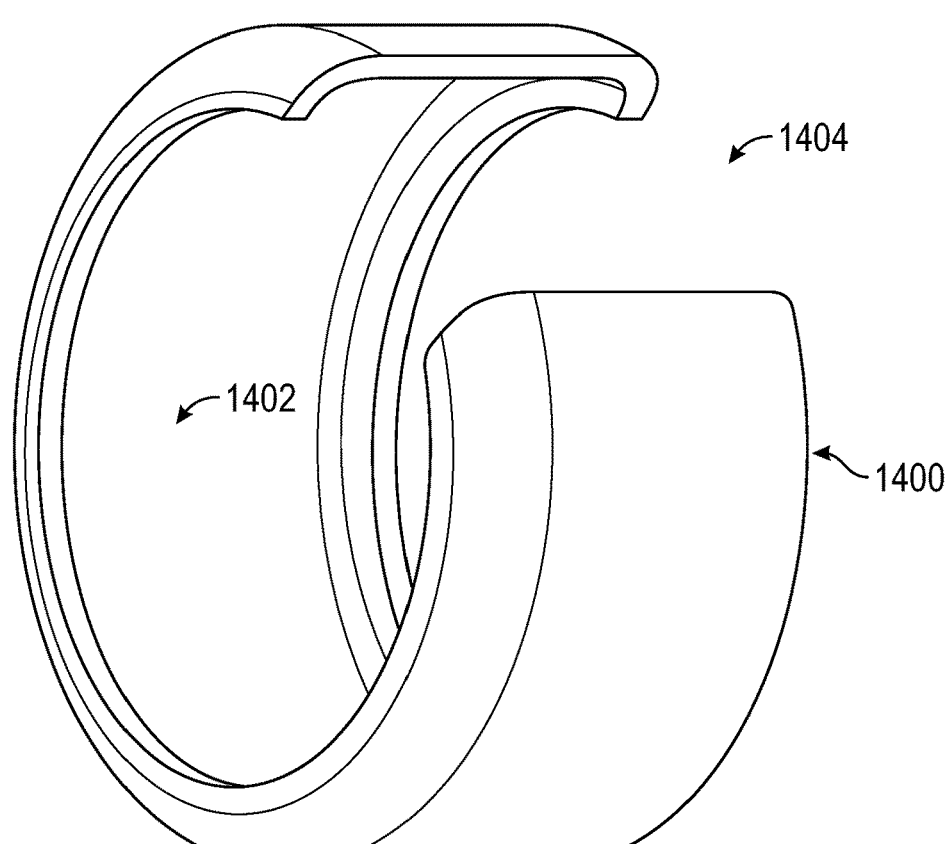
FIG. 15 illustrates an exemplary cap.

As illustrated in FIG. 14, a cap 1400 can be provided over the two rings 350, 360. The cap 1400 can assist in ensuring the connection between the rings 350, 360, as well as protecting the rings 350, 360 from external damage. As illustrated in FIG. 15, the cap 1400 can include a recess 1402 which is operable to receive the two rings 350, 360. An opening 1404 can be formed such that the cap 1400 can be deformed to snap over the two rings 350, 360.

Figure 16:
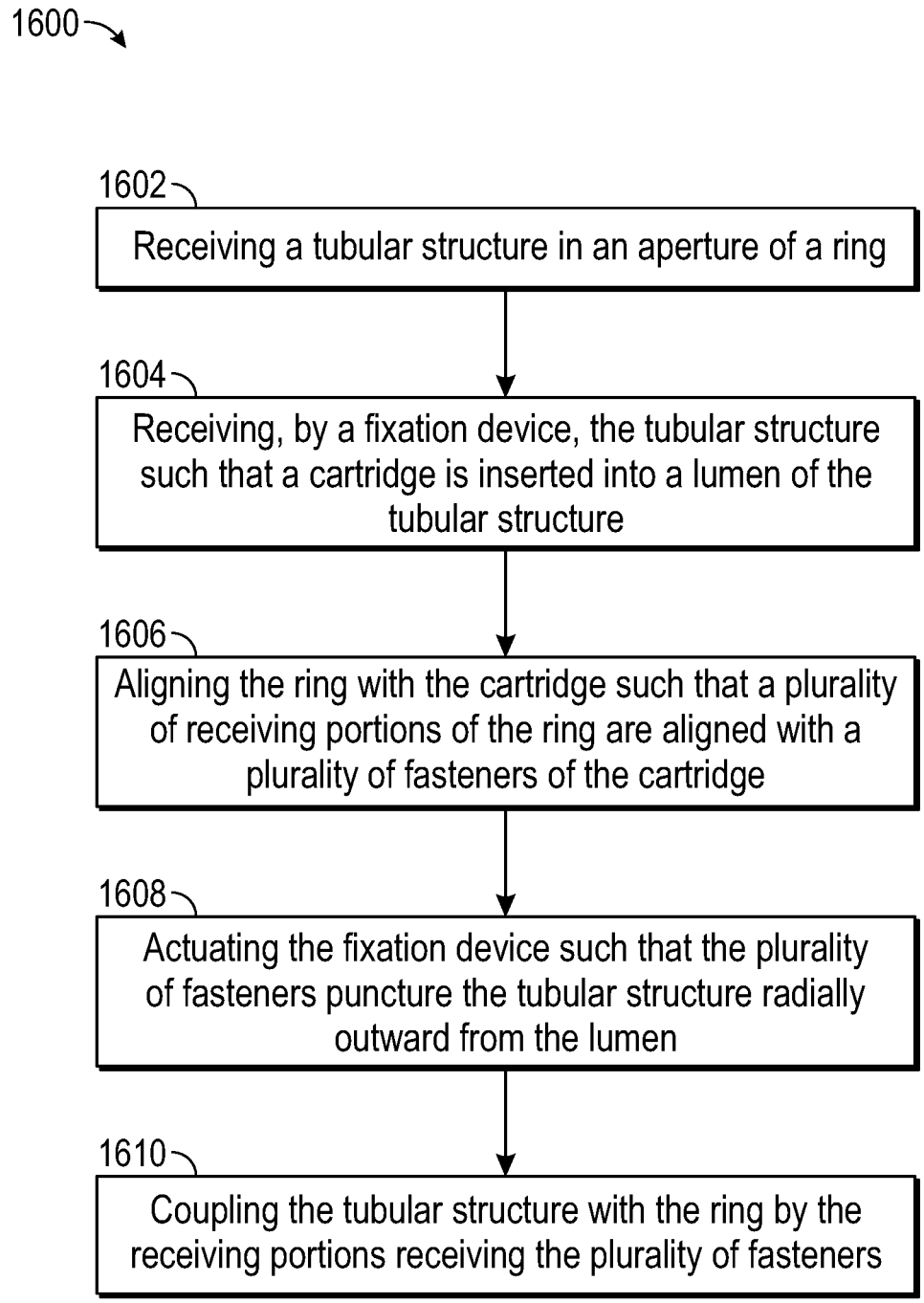
FIG. 16 is a flow chart of a method for utilizing an anastomotic coupler.

Referring to FIG. 16, a flowchart is presented in accordance with an example embodiment. The method 1600 is provided by way of example, as there are a variety of ways to carry out the method. The method 1600 described below can be carried out using the configurations illustrated in FIG. 1-15, for example, and various elements of these figures are referenced in explaining example method 1600. Each block shown in FIG. 16 represents one or more processes, methods or subroutines, carried out in the example method 600. Furthermore, the illustrated order of blocks is illustrative only and the order of the blocks can change according to the present disclosure. Additional blocks may be added or fewer blocks may be utilized, without departing from this disclosure. The example method 1600 can begin at block 1602.

At block 1602, a first tubular structure is received in an aperture of a first ring.

At block 1604, a fixation device receives the first tubular structure such that a first cartridge is inserted into a lumen of the first tubular structure.

At block 1606, the first ring is aligned with the first cartridge such that a plurality of receiving portions of the first ring are aligned with a plurality of fasteners of the first cartridge.

At block 1608, the fixation device is actuated such that the plurality of fasteners puncture the first tubular structure radially outward from the lumen. The cartridge can include a plurality of drivers corresponding with the plurality of fasteners. Upon actuation of the fixation device, the drivers activate to push the corresponding fasteners radially outward from the cartridge. In at least one example, the fixation device can include a pusher rod. The pusher rod can be tapered from a front portion with a smaller diameter to rear portion with a larger diameter. Upon actuation of the fixation device, the pusher rod can translate along a longitudinal axis to activate the drivers. In at least one example, to activate the drivers, the pusher rod translates along the longitudinal axis and passes through the cartridge from the front portion to the rear portion such that the pusher rod abuts and pushes the drivers and the corresponding fasteners radially outward from the cartridge.

At block 1610, the first tubular structure is coupled with the first ring by the receiving portions receiving the plurality of fasteners.

In at least one example, a second tubular structure can be received in an aperture of a second ring. A fixation device can receive the second tubular structure such that a second cartridge is inserted into a lumen of the second tubular structure. In at least one example, the fixation device may be the same fixation device that was utilized for the first ring. In some examples, the fixation device may be the same fixation device utilized for the first ring with a second cartridge that replaced the first cartridge. In some examples, the fixation device may be a second fixation device. The second ring can be aligned with the second cartridge such that a plurality of receiving portions of the second ring are aligned with a plurality of fasteners of the second cartridge. The fixation device can be actuated such that the plurality of fasteners puncture the second tubular structure radially outward from the lumen. The second tubular structure can be coupled with the second ring by the receiving portions receiving the plurality of fasteners.

The first ring can be aligned with the second ring such that the lumen of the first tubular structure and the lumen of the second tubular structure are aligned in fluid communication with one another. The first ring can be coupled with the second ring to join the first tubular structure with the second tubular structure, providing a continuous passage between the first tubular structure and the second tubular structure. In at least one example, a cap can be positioned about the first and the second ring to ensure the connection between the first ring and the second ring.

Numerous examples are provided herein to enhance understanding of the present disclosure. A specific set of statements are provided as follows.

Statement 1: An anastomotic coupler is disclosed comprising: a ring forming an aperture operable to receive a tubular structure, the ring including a plurality of receiving portions; a fixation deice including a housing and a cartridge, the cartridge including a plurality of fasteners, the housing operable to receive the tubular structure such that the cartridge is inserted into a lumen of the tubular structure, wherein the ring is aligned with the cartridge such that the plurality of receiving portions are aligned with the plurality of fasteners, wherein upon actuation of the fixation device, the plurality of fasteners puncture the tubular structure radially outward from the lumen and are received by the receiving portions such that the tubular structure is coupled with the ring.

Statement 2: An anastomotic coupler is disclosed according to Statement 1, wherein the fixation device includes a stop, the stop extending radially from the housing such that a free end of the tubular structure abuts the stop.

Statement 3: An anastomotic coupler is disclosed according to Statement 2, wherein the stop includes a plurality of alignment components corresponding with alignment components of the ring, wherein when the ring is aligned, the alignment components of the stop are aligned with the alignment components of the ring.

Statement 4: An anastomotic coupler is disclosed according to any of preceding Statements 1-3, wherein the cartridge includes a plurality of drivers corresponding with the plurality of fasteners, wherein upon actuation of the fixation device, the drivers activate to push the corresponding fasteners radially outward from the cartridge.

Statement 5: An anastomotic coupler is disclosed according to Statement 4, wherein the fixation device includes a pusher rod, wherein upon actuation of the fixation device, the pusher rod translates along a longitudinal axis to activate the drivers.

Statement 6: An anastomotic coupler is disclosed according to Statement 5, wherein the pusher rod is tapered from a front portion with a smaller diameter to rear portion with a larger diameter, wherein as the pusher rod translates along the longitudinal axis the pusher rod passes through the cartridge from the front portion to the rear portion such that the pusher rod abuts and pushes the drivers and the corresponding fasteners radially outward from the cartridge.

Statement 7: An anastomotic coupler is disclosed according to any of preceding Statements 1-6, wherein the plurality of fasteners include tacks, staples, pins, adhesive, internal ring, internal mesh, wire, clamp, coil, and/or suture.

Statement 8: A system is disclosed comprising: the anastomotic coupler of any of preceding Statements 1-7; a second ring forming an aperture operable to receive a second tubular structure having a lumen, the second ring coupled with the second tubular structure; wherein the ring and the second ring are coupled with one another and the tubular structure and the second tubular structure are joined such that the lumen of the tubular structure and the lumen of the second tubular structure are aligned in fluid communication with one another.

Statement 9: A system is disclosed according to Statement 8, wherein the first ring and the second ring create a seal to prevent fluid leakage.

Statement 10: A method is disclosed comprising: providing the anastomotic coupler of any of preceding Statements 1-7; receiving the tubular structure in the aperture of the ring; receiving, by the fixation device, the tubular structure such that the cartridge is inserted into the lumen of the tubular structure; aligning the ring with the cartridge such that the plurality of receiving portions of the ring are aligned with a plurality of fasteners of the cartridge; actuating the fixation device such that the plurality of fasteners puncture the tubular structure radially outward from the lumen; and coupling the tubular structure with the ring by the receiving portions receiving the plurality of fasteners.

Statement 11: A method is disclosed according to Statement 10, further comprising: receiving a second tubular structure in an aperture of a second ring; receiving, by the fixation device, the second tubular structure such that a second cartridge is inserted into a lumen of the second tubular structure; aligning the second ring with the second cartridge such that a plurality of receiving portions of the second ring are aligned with a plurality of fasteners of the second cartridge; actuating the fixation device such that the plurality of fasteners puncture the second tubular structure radially outward from the lumen; and coupling the second tubular structure with the second ring by the receiving portions receiving the plurality of fasteners.

Statement 12: A method is disclosed according to Statement 11, further comprising: aligning the first ring with the second ring such that the lumen of the first tubular structure and the lumen of the second tubular structure are aligned in fluid communication with one another; and coupling the first ring with the second ring to join the first tubular structure with the second tubular structure.

Statement 13: A method is disclosed according to any of preceding Statements 10-12, wherein the cartridge includes a plurality of drivers corresponding with the plurality of fasteners, wherein upon actuation of the fixation device, the drives activate to push the corresponding fasteners radially outward from the cartridge.

Statement 14: A method is disclosed according to Statement 13, wherein the fixation device includes a pusher rod; wherein the pusher rod is tapered from a front portion with a smaller diameter to rear portion with a larger diameter; wherein upon actuation of the fixation device, the pusher rod translates along a longitudinal axis to activate the drivers; wherein as the pusher rod translates along the longitudinal axis the pusher rod passes through the cartridge from the front portion to the rear portion such that the pusher rod abuts and pushes the drivers and the corresponding fasteners radially outward from the cartridge.

Statement 15: A method is disclosed according to any of preceding Statements 10-14, wherein the first ring and the second ring create a seal to prevent fluid leakage.

The disclosures shown and described above are only examples. Even though numerous properties and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

The invention claimed is:

1. An anastomotic coupler comprising:
   a ring forming an aperture operable to receive a tubular structure, the ring including a plurality of receiving portions;
   a fixation device including a housing and a cartridge, the cartridge including a plurality of fasteners, the housing operable to receive the tubular structure such that the cartridge is inserted into a lumen of the tubular structure,
   wherein the ring is aligned with the cartridge such that the plurality of receiving portions are aligned with the plurality of fasteners,
   wherein upon actuation of the fixation device, the plurality of fasteners puncture the tubular structure radially outward from the lumen and are received by the receiving portions such that the tubular structure is coupled with the ring.

2. The anastomotic coupler of claim 1, wherein the fixation device includes a stop, the stop extending radially from the housing such that a free end of the tubular structure abuts the stop.

3. The anastomotic coupler of claim 2, wherein the stop includes a plurality of alignment components corresponding with alignment components of the ring, wherein when the ring is aligned, the alignment components of the stop are aligned with the alignment components of the ring.

4. The anastomotic coupler of claim 1, wherein the cartridge includes a plurality of drivers corresponding with the plurality of fasteners, wherein upon actuation of the fixation device, the drivers activate to push the corresponding fasteners radially outward from the cartridge.

5. The anastomotic coupler of claim 4, wherein the fixation device includes a pusher rod, wherein upon actuation of the fixation device, the pusher rod translates along a longitudinal axis to activate the drivers.

6. The anastomotic coupler of claim 5, wherein the pusher rod is tapered from a front portion with a smaller diameter to a rear portion with a larger diameter.

7. The anastomotic coupler of claim 1, wherein the plurality of fasteners include tacks, staples, pins, adhesive, internal ring, internal mesh, wire, clamp, coil, and/or suture.

8. A system comprising:
   a first ring forming an aperture operable to receive a first tubular structure, the first ring including a plurality of receiving portions;
   a second ring forming an aperture operable to receive a second tubular structure, the second ring including a plurality of receiving portions;
   a fixation device including a housing and a cartridge, the cartridge including a plurality of fasteners, the housing operable to receive the first and/or second tubular structure such that the cartridge is inserted into a lumen of the corresponding first and/or second tubular structure,
   wherein the first and/or second ring is aligned with the cartridge such that the corresponding plurality of receiving portions are aligned with the plurality of fasteners,
   wherein upon actuation of the fixation device, the plurality of fasteners puncture the first and/or second tubular structure radially outward from the lumen and are received by the receiving portions such that the first tubular structure is coupled with the first ring and the second tubular structure is coupled with the second ring, wherein the first ring and the second ring are coupled with one another and the first tubular structure and the second tubular structure are joined such that the lumen of the first tubular structure and the lumen of the second tubular structure are aligned in fluid communication with one another.

9. The system of claim 8, wherein the first ring and the second ring create a seal to prevent fluid leakage.

10. The system of claim 8, wherein the cartridge includes a plurality of drivers corresponding with the plurality of fasteners, wherein upon actuation of the fixation device, the drivers activate to push the corresponding fasteners radially outward from the cartridge.

11. The system of claim 10, wherein the fixation device includes a pusher rod, wherein upon actuation of the fixation device, the pusher rod translates along a longitudinal axis to activate the drivers.

12. The anastomotic coupler of claim 11, wherein the pusher rod is tapered from a front portion with a smaller diameter to a rear portion with a larger diameter.

13. The system of claim 8, wherein the plurality of fasteners include tacks, staples, pins, adhesive, internal ring, internal mesh, wire, clamp, coil, and/or suture.

14. A method comprising:
receiving a tubular structure in an aperture of a ring;
receiving, by a fixation device, the tubular structure such that a cartridge is inserted into a lumen of the tubular structure;
aligning the ring with the cartridge such that a plurality of receiving portions of the ring are aligned with a plurality of fasteners of the cartridge;
actuating the fixation device such that the plurality of fasteners puncture the tubular structure radially outward from the lumen; and
coupling the tubular structure with the ring by the receiving portions receiving the plurality of fasteners.

15. The method of claim 14, further comprising:
receiving a second tubular structure in an aperture of a second ring;
receiving, by a fixation device, the second tubular structure such that a second cartridge is inserted into a lumen of the second tubular structure;
aligning the second ring with the second cartridge such that a plurality of receiving portions of the second ring are aligned with a plurality of fasteners of the second cartridge;
actuating the fixation device such that the plurality of fasteners puncture the second tubular structure radially outward from the lumen; and
coupling the second tubular structure with the second ring by the receiving portions receiving the plurality of fasteners.

16. The method of claim 15, further comprising:
aligning the ring with the second ring such that the lumen of the first tubular structure and the lumen of the second tubular structure are aligned in fluid communication with one another; and
coupling the ring with the second ring to join the tubular structure with the second tubular structure.

17. The method of claim 14, wherein the cartridge includes a plurality of drivers corresponding with the plurality of fasteners, wherein upon actuation of the fixation device, the drivers activate to push the corresponding fasteners radially outward from the cartridge.

18. The method of claim 17, wherein the fixation device includes a pusher rod; wherein the pusher rod is tapered from a front portion with a smaller diameter to a rear portion with a larger diameter, wherein upon actuation of the fixation device, the pusher rod translates along a longitudinal axis to activate the drivers.

* * * * *